US005349095A

United States Patent [19]

Thomas et al.

[11] Patent Number: 5,349,095
[45] Date of Patent: Sep. 20, 1994

[54] PROCESS FOR PREPARING HYDROXYALKYLBENZOCYCLOBUTENES

[75] Inventors: P. J. Thomas; R. Garth Pews, both of Midland, Mich.

[73] Assignee: The Dow Chemical Company, Midland, Mich.

[21] Appl. No.: 982,213

[22] Filed: Nov. 25, 1992

Related U.S. Application Data

[63] Continuation-in-part of Ser. No. 861,693, Apr. 1, 1992, abandoned.

[51] Int. Cl.$^5$ .............................................. C07C 29/14
[52] U.S. Cl. .................................... 568/814; 568/323
[58] Field of Search ................................ 568/323, 814

[56] References Cited

U.S. PATENT DOCUMENTS

| | | | |
|---|---|---|---|
| 2,694,730 | 11/1954 | Ipatieff et al. | 568/323 |
| 3,408,391 | 10/1968 | Skorcz | 568/323 |
| 3,859,364 | 1/1975 | Wilson | 568/323 |
| 4,540,763 | 9/1985 | Kirchhoff | 568/323 |
| 4,708,990 | 11/1987 | Wong et al. | 568/323 |
| 4,708,994 | 11/1987 | Wong | 568/322 |

OTHER PUBLICATIONS

J. B. F. Lloyd and P. A. Ongley, *Tetrahedron Letters*, "The Electrophilic Substitution of Benzocyclobutene-II: Benzoylation, Sulphonation, Bromination and Chlorination," No. 21, pp. 245–254, Pergamon Press, 1965.
J. Michael Riemann and Walter S. Trahanovsky. *Tetrahedron Letters*, "Formation of Cyclobuta[b]pyridine and Cyclobuta[c]pyridine by the Pyrolysis of Propargyl 4-pyridyl Ether" No. 22, pp. 1867–1870, Pergamon Press, 1977.
J. B. F. Lloyd and P. A. Ongley. *Tetrahedron Letters*, "The Electrophilic Substitution of Benzocyclobutene-I: Nitration, Acetylation and Hyrdrobromination," vol. 20, pp. 2185–2194. Pergamon Press Ltd. (1964).
S. Wattanasin and F. G. Kathawala. *Tetrahedron Letters*, "Convenient Ketone Synthesis Via N-Acylaziridines," vol. 25, No. 8, pp. 811–814. (1984).
W. D. Crow et al, *Australian Journal of Chemistry*, "The $C_6H_5N$ Energy Surface. III, IV, and V". vol. 28, pp. 1741–1773, (1975).
E. A. Evans. *J. Chem. Soc.*, "The Preparation of Aliphatic Aldehydes and Ketones from Lithium Alkyls and Dimethylamides" pp. 4691–4693. (1956).
Rieche et al. *Organic Syntheses*, "Aromatic Aldehydes. Mesitaldehyde," Col. Vol. V, pp. 49–51. (1973).
S. W. Chaikin et al. *J. Am. Chem. Soc.*, "Reduction of Aldehydes, Ketones and Acid Chlorides by Sodium Borohydride," vol. 71, pp. 122–125. (1949).
P. J. Thomas et al. *Synthetic Communications*, "A Facile Synthesis of Bicyclo[4.2.0]ocat-1,3,5-trien-3-ol," vol. 21, pp. 2335–2340. (Dec. 1991).
K. P. C. Vollhardt et al. *J. Am. Chem. Soc.*, "A One-Step Synthesis of Benzocyclobutenes Involving Cooligomerization of Linear Mono- and Diacetylenes Catalyzed by $\eta^5$-Cyclopentadienylcobalt Dicarbonyl," vol. 96, pp. 4996–4998. (1974).

*Primary Examiner*—James H. Reamer
*Attorney, Agent, or Firm*—Charlotte M. Kraebel; Charles J. Enright

[57] ABSTRACT

A process for preparing a substituted or unsubstituted 3- or 4-hydroxyalkylbenzocyclobutene compound comprises reducing a corresponding 3- or 4-formyl or ketobenzocyclobutene compound with a hydride at a temperature below that at which dimerization or oligomerization of the formyl- or ketobenzocycloutene compound or the thus-produced hydroxyalkylbenzocyclobutene compound is a significant side reaction, for a time sufficient to convert the formyl- or ketobenzocyclobutene compound to the hydroxyalkylbenzocyclobutene compound. In a two-step process, formylbenzocyclobutenes are prepared from bromobenzocyclobutenes in 90% yield or from benzocyclobutenes in a 70% yield, and then converted to hydroxymethylbenzocyclobutenes for an overall yield of about 85% from a bromobenzocyclobutene or of about 65% from a benzocyclobutene. In a two-step process, ketobenzocyclobutenes from bromobenzocyclobutene Grignard reagents and an N-alkanoyl- or N-aroyl-2-methylaziridine are converted to hydroxyalkylbenzocyclobutenes in high yields.

11 Claims, No Drawings

PROCESS FOR PREPARING HYDROXYALKYLBENZOCYCLOBUTENES

Reference to Related Application

This Application is a continuation-in-part of application Ser. No. 07/861,693, filed Apr. 1, 1992 now abandoned.

TECHNICAL FIELD

This invention relates to a low temperature, high yield process for preparing hydroxyalkylbenzocyclobutenes, particularly hydroxymethylbenzocyclobutene, which is useful as an intermediate for producing specialty polymers. A low temperature process for preparing these intermediates is highly important, because benzocyclobutenes tend to polymerize through ring opening to ortho-xylylene moieties at high temperatures.

BACKGROUND ART

Vollhardt et al., J. Am. Chem. Soc., vol 96 (1974), pages 4996-4998, have disclosed the synthesis of 4-hydroxymethylbenzocyclobutene by a cyclization process, which gives a 14% yield of the desired product.

Wong (U.S. Pat. No. 4,708,994) has proposed using 4-hydroxymethylbenzocyclobutene to treat engineering thermoplastics, which may then be crosslinked and cured by heating above about 200° C.

Skorcz (U.S. Pat. No. 3,408,391) has recited the preparation of 1-hydroxymethylbenzocyclobutene by reducing benzocyclobutene-1-carboxylic acid with lithium aluminum hydride in an anhydrous reaction medium, such as ether or tetrahydrofuran. The intermediate complex alcoholate is hydrolyzed by treatment with an acid to produce 1-hydroxymethylbenzocyclobutene.

Wilson (U.S. Pat. No. 3,859,364) has proposed reducing indane esters using lithium aluminum hydride.

Vanderwerff (U.S. Pat. No. 3,288,823) has proposed reducing 2,6-naphthalenedicarboxaldehyde to 2,6-bis(-hydroxymethyl)naphthalene using excess sodium borohydride in ethanol.

Chaikin et al., J. Am. Chem. Soc., vol. 71 (1949), pages 122-125, have summarized the reduction of aldehydes and ketones by sodium borohydride in aqueous or methanolic solutions.

Ipatieff et al. (U.S. Pat. No. 2,694,730) has recited reduction of 2-formyl-6-hydrocarbylbicyclo-[3.2.1]-2-octenes to corresponding 2-alcohols by catalytic hydrogenation.

Disclosure of the Invention

This invention relates to a process for preparing a substituted or unsubstituted 3- or 4-hydroxyalkylbenzocyclobutene compound, comprising reducing a corresponding 3- or 4-formyl- or ketobenzocyclobutene compound with a hydride selected from sodium borohydride, lithium aluminum hydride or NaBH$_3$CN at a temperature below that at which dimerization or oligomerization of the formyl-or ketobenzocyclobutene compound or the thus-produced hydroxyalkylbenzocyclobutene compound is a significant side reaction, for a time sufficient to convert the formyl- or ketobenzocyclobutene compound to the hydroxyalkylbenzocyclobutene compound.

This invention further relates to a two-step process for the preparation of hydroxyalkylbenzocyclobutene compounds wherein the first step comprises:

(a) reaction between a Grignard reagent obtained from a substituted or unsubstituted 3- or 4-bromobenzocyclobutene compound and dimethylformamide to produce an intermediate formylbenzocycloutene compound;

(b) reaction between a substituted or unsubstituted benzocyclobutene compound and dichloromethyl methyl ether in the presence of titanium tetrachloride to produce an intermediate formylbenzocyclobutene compound or (c) reaction between a Grignard reagent obtained from a substituted or unsubstituted 3- or 4-bromobenzocyclobutene compound and an N-alkanoyl- or N-aroyl-2-methylaziridine compound to produce an intermediate ketobenzocyclobutene compound.

"Benzocyclobutene," as used in the specification and claims, includes carbocyclic and heterocyclic arylcyclobutene (cyclobutarene) compounds, which consist of a cyclobutene ring fused to an aromatic carbocyclic or hetercyclic ring. Aromatic as used herein refers to carbocyclic or heterocyclic rings in which 4 n+2 delocalized pi electrons are contained in an orbital ring. This property is also known as resonance stabilization or delocalization.

Preferred carbocyclic aromatic moieties include benzene, naphthalene, phenanthrene, anthracene, a biaryl moiety or two or more aromatic radicals, bridged by alkylene or cycloalkylene moieties. More preferred carbocyclic aromatic radicals include benzene, naphthalene, biphenyl, binaphthyl, diphenylalkane or diphenylcycloalkane radicals. The most preferred carbocyclic aromatic radical is a benzene radical, which, when fused to a cyclobutene ring, produces the simplest member of the series, benzocyclobutene.

Examples of preferred heterocyclic aromatic compounds include pyrrole, furan, thiophene, imidazole, oxazole, thiazole, pyrazine, pyridine and pyrimidine. More preferred heterocyclic aromatic radicals are pyridine, furan and thiophene, with cyclobutapyridine being most preferred. The carbocyclic analogs are preferred over the heterocyclic analogs.

Either the aryl radical or the cyclobutene ring can be substituted by electron-donating or electron-withdrawing groups, provided that the substituent is not reduced by the sodium borohydride. Examples of such substituents include cyano, halo, carboxy, hydrocarbyloxy, alkylsulfonyl, alkylsulfonoyl, amido, alkyl, alkenyl or aryl groups.

It will be understood that "benzocyclobutene" is an art-recognized term. In the commonly-used non-systematic numbering system for benzocyclobutenes, the 1- and 2-positions are in the cyclobutene ring. The 3- and 6-positions are in an aromatic ring, adjacent to the cyclobutene ring. The 4- and 5-positions are meta- to the cyclobutene ring. The simplest member of the series, benzocyclobutene, is formally identified as bicyclo[4.2.0]octa-1,3,5-triene. A compound, formally identified as 3-hydroxymethylbicyclo[4.2.0]octa-1,3,5-triene, is commonly known as 4-hydroxymethylbenzocyclobutene. The common names will be used in the specification and claims.

The process of this invention can be represented, when sodium borohydride is the reducing agent, by the equation:

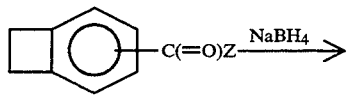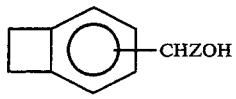

wherein Z is H, alkyl, aryl, or alkaryl, including substituted and heterocyclic derivatives. When Z=H, the products are hydroxymethylbenzocyclobutenes and when Z is other than H, the products are secondary alcohols.

The hydroxyalkylbenzocyclobutene products of this invention can be used for the preparation of bridged benzocyclobutenes, characterized for the sake of simplicity as hydroxymethylbenzocyclobutene derivatives of the formula

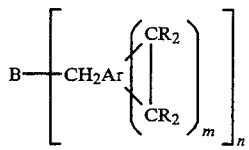

wherein B is an n-valent bridging moiety containing oxygen, bonded to the aromatic ring (Ar) of the benzocyclobutene unit by an intervening methylene moiety, m is an integer of 1 or more, n is an integer of 2 or more and each R is hydrogen or an electron-donating or electron-withdrawing substituent.

In the simplest cases, the cyclobutene ring is unsubstituted (each R is H and m is 1) and the aromatic ring is benzene. This case can be represented by the subgeneric formula

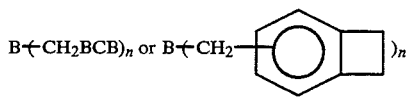

wherein B is the oxygen-containing bridging function and n is as above. In this formula, BCB represents 3- or 4-benzocyclobutenyl.

Examples of oxygen-containing bridging groups include, but are not limited to,

—O(C=O)NH—, —O(C=O)O—, —O—,
—O—Q—O—, —O(C=O)—Q—(C=O)O—,
—O—(C=O)— or
—O(C=O)—O—Q—O(C=O)O— wherein Q is a divalent bridging group, such as phenylene, xylylene, tolylene, arylene-alkylene-arylene, alpha,omega-alkylene and the like.

A particularly preferred bridging group is the carbonate group. In the simplest case, the product is of the formula

BCBCH$_2$—O—(C=O)—O—CH$_2$BCB.

Other carbonates are those derived, for example, from diphenolic compounds, such as hydroquinone or bisphenol A. These are represented by the formulas

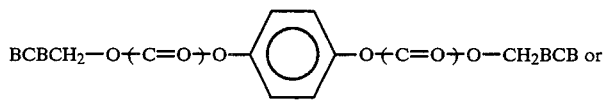

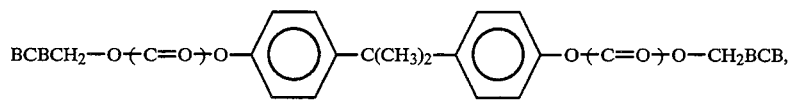

respectively.

Other preferred bridging groups include ester groups, such as terephthaloyloxy or adipoyloxy, which produce bridged derivatives of the formulas

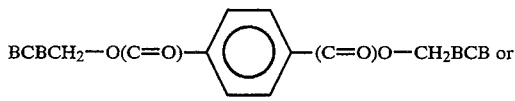

respectively.

Another preferred type of bridging group is that wherein Q is alkylene and the simplest products correspond to the general formula BCBCH$_2$—O—C$_x$H$_{2x}$O—CH$_2$BCB in which x is an integer from 2–20. Most preferred bridging groups include those derived by reaction with an alkylene glycol, such as 1,4-butanediol or 1,6-hexanediol.

Corresponding oxaalkylene glycols can be used as bridging groups. For example, B can be —OC$_{x/2}$H$_x$OC$_{x/2}$H$_x$O—, wherein x is as above. Other oxygen-containing bridging groups are disclosed by Kirchhoff et al., U.S. Pat. Nos. 4,540,763 and 4,999,449, herein incorporated by reference.

Exemplary unbridged formylbenzocyclobutene compounds which can be converted to hydroxymethylbenzocyclobutenes in accordance with this invention include, but are not limited to, compounds of the structures:

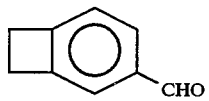

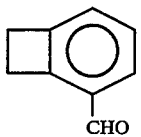

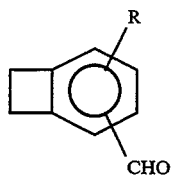

wherein R is alkyl, vinyl, substituted vinyl, ethinyl, substituted ethinyl, aryl, polyaryl, substituted aryl, substituted polyaryl, heterocyclic, heteroaryl, alkylaryl, alkylheterocyclic, arylheteroaryl, trialkylsilyl, nitro, cyanato, benzobicyclobutenyl, alkylbenzocyclobutenyl, arylbenzocyclobutenyl, alkylarylbenzocyclobutenyl, arylalkylbenzocyclobutenyl, oxybenzocyclobutenyl, thiobenzocyclobutenyl, benzocyclobutenyl sulfonyl, benzocyclobutenyl sulfoxide, alkoxy, aryloxy, substituted alkoxy, substituted aryloxy, polyaryloxy, substituted polyaryloxy, alkylthio, substituted alkylthio, arylthio, substituted arylthio, polyarylthio, substituted polyarylthio, heterocyclothio and heteroarylthio. Substituted compounds include hydrocarbyl substituents, as recited by Kirchhoff, supra.

Representative higher fused ring benzocyclobutene reactants include, but are not limited to, compounds of the formulas:

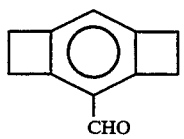

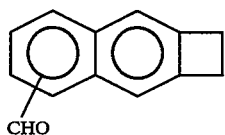

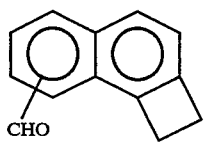

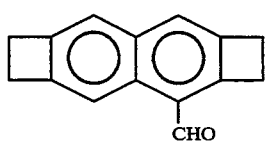

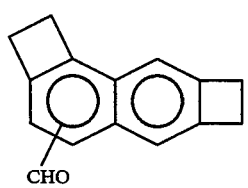

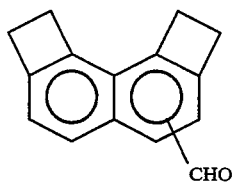

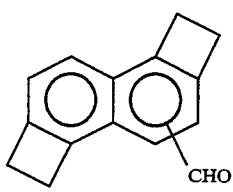

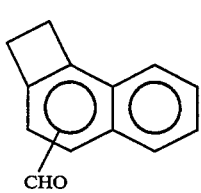

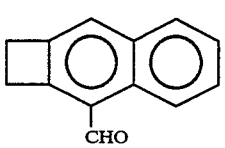

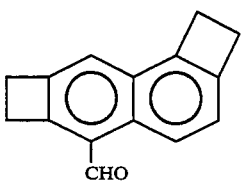

It will be understood that the fused ring benzocyclobutenes can be substituted as above and that diformyl or diketo compounds can also be used.

Preferred reactants for the practice of this invention are those containing a 3- or 4-formylbenzocyclobutene moiety, more preferably a 4-formylbenzocyclobutene moiety. The most preferred benzocyclobutene reactant is 4-formylbenzocyclobutene.

4-Formylbenzocyclobutene is a known compound, the synthesis of which is recited by Wong et al., U.S. Pat. No. 4,708,990, herein incorporated by reference. This reference describes the treatment of 4-chloromethylbenzocyclobutene with hexamethylene tetramine and sodium iodide in ethanol to given an unspecified yield of formylbenzocyclobutene.

Bromobenzocyclobutenes are known compounds. A typical synthesis of a representative bromobenzocyclobutene compound, 4-bromobenzocyclobutene, is presented by Kirchhoff '449, supra.

Ketobenzocyclobutenes can be prepared by in low yields by Friedel-Crafts acylation or aroylation. Preparation of 4-acetylbenzocyclobutene is reported by Lloyd et al., *Tetrahedron*, vol. 20, pages 2185–2194 (1964) and of 4-benzoylbenzocyclobutene by Lloyd et al., *Tetrahedron*, vol 21, pages 245–254 (1965).

A process for preparing benzocyclobutenyl ketones in higher yields comprises the steps of:

(a) reacting a substituted or unsubstituted 3- or 4-bromobenzocyclobutene compound with magnesium to produce a corresponding 3- or 4-benzocyclobutenyl magnesium bromide and (b) treating the thus-formed 3- or 4-benzocyclobutenyl magnesium bromide with a 1-alkanoyl- or 1-aroyl-2-methylaziridine compound to produce a corresponding 3- or 4-alkanoyl or -aroylbenzocyclobutene.

A representative synthesis is that of 4-acetylbenzocyclobutene (70% yield):

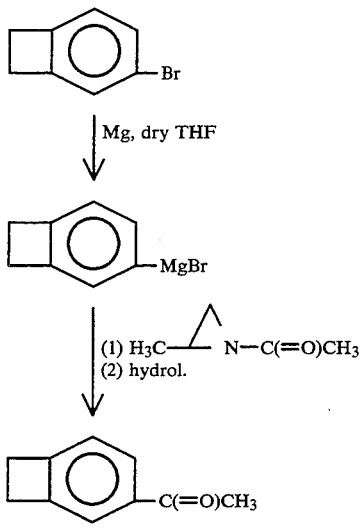

The stoichiometry for the reaction between the bromobenzocyclobutene compound and magnesium is generally from 1 to 2 moles of magnesium per mole of bromobenzocyclobutene compound. Preferably, from about 1.2 to about 1.7 mole of magnesium is used per mole of bromobenzocyclobutene compound.

The reaction can be initiated by adding about one fourth of the bromobenzocyclobutene compound to magnesium and solvent and warming the mixture to about 40°–50° C. The remainder of the benzocyclobutene compound is added in portions, so as to prevent an exothermic reaction.

If desired, the Grignard reaction can be started using an initiator. The initiator for the Grignard reaction can be selected from those known in the art, including, but not limited to, methyl iodide, ethyl bromide, dibromoethane and dibromopropane. The Grignard reagents are prepared in dry solvents, of which diethyl ether and tetrahydrofuran are preferred.

It will be understood that corresponding iodobenzocyclobutene compounds can be used instead of bromobenzocyclobutene compounds for the preparation of the Grignard reagents.

In the reaction between the Grignard reagent and the alkanoyl- or aroyl-2-methylaziridine compound, it is preferred to use from about 1 mole to about 2 moles of aziridine compound to Grignard reagent. Most preferably, from about 1.5 moles to about 1.9 moles of aziridine compound are used for each mole of Grignard reagent.

The ketone product is isolated by standard techniques, for example, by hydrolysis with dilute hydrochloric acid.

It will be understood that representative alkanoyl groups include, but are not limited to, acetyl, propionyl, butyryl or hexanoyl and that representative aroyl groups include, but are not limited to, benzoyl, toluoyl or naphthoyl.

In one improved two-step process for the preparation of hydroxymethylbenzocyclobutenes, the intermediate formylbenzocyclobutene compound is made from a Grignard reagent, obtained from a bromobenzocyclobutene compound and magnesium, and the Grignard reagent is treated with dimethylformamide to produce a corresponding formylbenzocyclobutene compound in 90% yield. This process is disclosed by Thomas et al., *Synthetic Communications*, vol. 21 (December, 1991), pages 2335-2340.

A typical reaction can be represented by the equation:

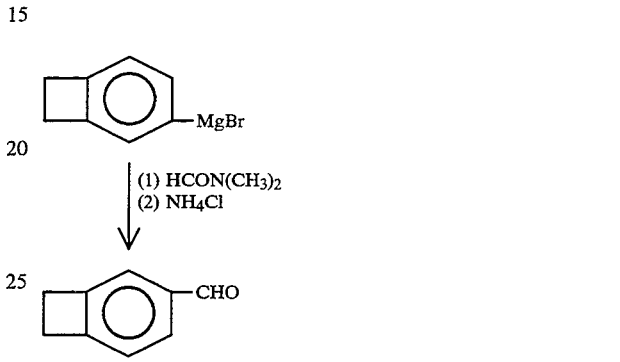

The ratios of reactants are within the same ranges as disclosed for the ketone synthesis, using N-alkanoyl or N-aroyl-2-methylaziridines. Similar solvents are used. The products are isolated by hydrolyzing the resulting intermediate organometallic complexes by known methods, for example, by pouring the reaction mixture into ammonium chloride solution.

Alternatively, a formylbenzocyclobutene intermediate is made from a benzocyclobutene compound by reaction with dichloromethyl methyl ether in the presence of titanium tetrachloride in methylene chloride. A typical yield for this route to the intermediate formylbenzocyclobutene compound is 70%. See Thomas et al, supra, and Rieche et al., *Org. Syn.*, Coll. Vol. V (1973), pages 49-51.

This reaction can be represented by the equation:

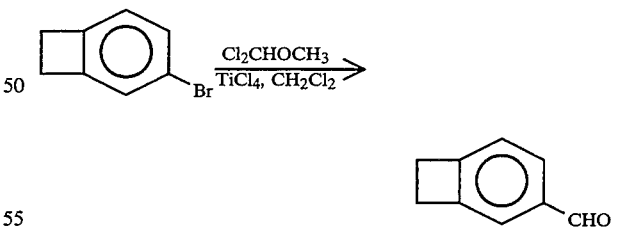

In this route to formylbenzocyclobutenes, from about 1 mole to about 1.5 moles of dichloromethyl methyl ether can be used per mole of benzocyclobutene compound. It is preferred to use from about 1.1 moles to about 1.2 moles of dichloromethyl methyl ether per mole of benzocyclobutene compound.

Titanium tetrachloride is the preferred reagent. Tin tetrachloride can also be used as reagent for this reaction. The starting benzocyclobutene compound can be selected from compounds, which do not react with the catalyst. These compounds generaly include substitued or unsubstituted benzocyclobutene compounds, except for those substituted with hydroxyl, carboxyl, amino or sulfhydryl moieties.

The reactions are carried out in a solvent, which is inert with respect to the reactants, catalyst and products. The reaction solvent can be selected from hydrocarbon or halogenated hydrocarbon solvents, including but not limited to ligroins, petroleum ethers, toluene, methylene chloride, methyl chloride, trichloromethane and the like. Methylene chloride is the preferred solvent.

The reduction of a formyl- or ketobenzocyclobutene employs as reducing agent sodium borohydride, lithium aluminum hydride or NaBH$_3$CN (at pH about 4). Sodium borohydride is the preferred reducing agent for the practice of this invention.

It is preferred to use at least a small excess of sodium borohydride or other reducing agent for the reduction. Preferably, from about 0.3 mole to about 1.5 mole of sodium borohydride is used for each mole of formyl- or ketobenzocyclobutene.

The process using sodium borohydride can be carried out in an alcoholic or aqueous solvent, or mixed solvent. Suitable solvents include ethanol, isopropanol, or tetrahydrofurfuryl alcohol, alone or mixed with water. Aqueous solutions can be used, provided that sodium hydroxide is added to stabilize the sodium borohydride. It is preferred to use ethanol as solvent. If lithium aluminum hydride is used as reducing agent, it is preferred to use an ether, such as diethyl ether or tetrahydrofuran, as solvent. The volume of solvent is generally varied from about 5 mL to about 50 mL per gram of starting material.

The reduction can be carried out at room temperature. If it is found that a reduction using a given starting material is highly exothermic, the reaction mixture can be cooled with an ice bath.

The time required for conversion of a formyl- or ketobenzocyclobutene to hydroxyalkylbenzocyclobutene is a function primarily of the reaction temperature and the amount of sodium borohydride used and can be determined empirically.

At the end of the reaction, solvent is removed. The dry residue is taken up in water and extracted into an organic solvent, e.g. ethyl acetate. The ethyl acetate solution is washed with water and brine and dried over an anhydrous salt. 4-Hydroxymethylbenzocyclobutene can be recrystallized from hot hexanes.

The process of converting formylbenzocyclobutenes to hydroxymethylbenzocyclobutenes in a direct one-step process is particularly advantageous because the low reaction temperature results in a very low degree of oligomerization or polymerization. The yields of the one-step reaction generally exceed 90% or 95%.

The process of this invention can be carried out in any container, with or without a stirring attachment, which is not attacked by the reactants or products of the invention.

Cyclobutapyridines can be prepared by the pyrolysis of 4-pyridyl propargyl ether at 550° C. See J. M. Riemann et al., *Tetrahedron Letters*, no. 22 (1977), pages 1867–1870. Alternatively, a pyridine-4-carbonitrile, having an alkyl substituent on the carbon atom adjacent to the nitrile, is reacted with sodium azide and ammonium chloride in N,N-dimethylformamide to prepare a 5-(alkyl-4-pyridyl)tetrazole. The 5-(alkyl-4-pyridyl)tetrazole is pyrolyzed at about 600° C. to a cyclobutapyridine. See W. D. Crow et al., *Austrailian Journal of Chemistry* (1975), after page 1741. 2-Bromocyclobuta[b-]pyridine can be prepared from 2-hydroxy[b]cyclobutapyridine. See Kirchoff et al., U.S. Pat. No. 4,783,514, herein incorporated by reference.

BEST MODE FOR CARRYING OUT THE INVENTION

Most preferably, the process of this invention is that wherein the formylbenzocyclobutene compound is 4-formylbenzocyclobutene; the 4-formylbenzocyclobutene is prepared from 4-bromobenzocyclobutene Grignard reagent by reaction with dimethylformamide in tetrahydrofuran; the reducing agent for the 4-formylbenzocyclobutene is sodium borohydride; and 4-formylbenzocyclobutene is reduced in ethanol at a temperature near ambient.

Without further elaboration it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the following examples, the temperatures are set forth uncorrected in degrees Celsius. Unless otherwise indicated, all parts and percentages are by weight.

EXAMPLE 1

Preparation of Benzocylclobutenyl Ketones (a) Preparation of 1-Acetyl-2-methylaziridine The procedure of Wattanasin et al., *Tetrahedron Letters*, vol. 25, page 811 (1984), is followed. Acetyl chloride (78.5 g) is added slowly over 30 min to a solution of 63 g of 2-methylaziridine (Aldrich) and 111 g of triethylamine in 200 mL of pentane at 0° C. The solution is stirred at 0° C. for 30 min, diluted with pentane and filtered. Solvent is distilled from the filtrate. The residue is distilled under vacuum. The product boils at 30° C./3 mm.

(b) Preparation of 4-Acetylbenzocyclobutene

Grignard reagent is prepared from 9.1 g of 4-bromobenzocyclobutene and 2 g of magnesium turnings in tetrahydrofuran. About one fourth of the 4-bromobenzocycloutene is added to a suspension of magnesium turnings in tetrahydrofuran. The resulting mixture is gently heated to 40°–50° C. to start the reaction. The remainder of the 4-bromobenzocyclobutene is added slowly, so as to avoid an exothermic reaction. At the end of the addition, the mixture is stirred for about an hour.

The thus-prepared Grignard reagent is added dropwise to a solution of 9.5 g of 1-acetyl-2-methylaziridine in tetrahydrofuran at 0° C. The resulting mixture is allowed to warm to room temperature and stirred for 2 h. The organomagnesium complex is hydrolyzed with dilute hydrochloric acid.

Solvent is removed from the resulting organic layer. The residue is distilled under vacuum to give 12 g of 4-acetylbenzocyclobutene, boiling at 90° C./1 mm.

EXAMPLE 2

Bicyclo[4.2.0] octa-1,3,5-triene-3-carboxaldehyde (4 Formylbenzocyclobutene)

(a) From 4-Bromobenzocyclobutene

The procedure is that of Evans, *J. Chem. Soc.* (1956), pages 4691–4693. Dimethylformamide (15 mL) is added dropwise to a stirred solution of Grignard reagent prepared from 4.8 g of magnesium and 18.3 g of 4- bromobenzocyclobutene in 40 mL of tetrahydrofuran at 0° C. under a nitrogen atmosphere. The resulting mixture is warmed slowly to room temperature and poured into 100 mL of saturated ammonium chloride solution. The mixture is extracted with ethyl acetate and the organic extract is washed with water and brine and then dried over anhydrous magnesium sulfate. After removing solvent, the product is distilled under reduced pressure to give 11.9 g (90%) of 4-formylbenzocyclobutene, b 90° C./3.5 mm.

IR (neat): 2930, 2820, 2730, 1685, 1595 cm$^{-1}$. $^1$H-NMR (CDCl$_3$) δ 9.94 (s, 1H), 7.73 (d, J=7.53 Hz, 1H), 7.57 (s, 1H), 7.21 (d, J=7.53 HZ, 1H) and 3.24 (s, 4H). $^{13}$C-NMR (CHCl$_3$) δ 193.00, 154.10, 146.89, 135.95, 130.61, 123.10, 123.04, 29.84 and 29.11. HRMS: m/e 132.0579 (calc'd for C$_9$H$_8$O, 132.0575).

(b) From Benzocyclobutene

The procedure is that of Rieche et al., *Org. Syn.* Coll. Vol. V (1973), pages 49–51. To a stirred solution of 2.08 g of benzocyclobutene in 25 mL of methylene chloride at 0° C. is added 7.26 g of titanium tetachloride over a period of 10 min. At the end of the addition, 2.3 g of dichloromethyl methyl ether in 5 mL of methylene chloride is added dropwise.

The resulting mixture is stirred for one h more at 0° C. and poured into 100 g of crushed ice. The mixture is extracted with ethyl acetate and worked up as in (a) to give 1.85 g (70%) of the aldehyde. Physical properties and spectra of the product are identical with those of the material prepared in (a).

EXAMPLE 3

To a stirred solution of 1.32 g of 4-formylbenzocyclobutene in 15 mL of ethanol at room temperature is added 0.38 g of sodium borohydride. The reaction mixture is stirred for 2 h at room temperature. Ethanol is removed using a rotary evaporator and the residual material is diluted with 50 mL of water.

The aqueous mixture is extracted with ethyl acetate. The ethyl acetate layer is washed with water and with saturated sodium chloride brine and dried over anhydrous magesium sulfate. The solution is filtered and solvent is removed from the filtrate. The yield of 4-hydroxymethylbenzocyclobutene is 1.27 g (95%, m.p. 70° C. from hexanes).

EXAMPLE 4

4-Acetylbenzocyclobutene is reduced with sodium borohydride in 2 me ethanol. 1-(4-Benzocyclobutenyl)-benzyl alcohol is obtained.

EXAMPLE 5

4-Benzoylbenzocyclobutene is reduced with sodium borohydride in 2$^n$ ethanol. 1-(4-Benzocyclobutenyl)benzyl alcohol is obtained.

EXAMPLE 6

4-Formylbenzocyclobutene is reduced with sodium borohydride in water, containing 1% by weight of sodium hydroxide. 4-Hydroxymethylbenzocyclobutene is obtained.

EXAMPLE 7

4-Formylbenzocyclobutene is reduced with sodium borohydride in tetrahydrofurfuryl alcohol solvent. Similar results are obtained.

EXAMPLE 8

4-Formylbenzocyclobutene is reduced with lithium aluminum hydride in dry diethyl ether. Similar results are obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for preparing a substituted or unsubstituted 3- or 4-hydroxymethylbenzocyclobutene compound, comprising reducing a corresponding 3-or 4-formylbenzocyclobutene compound with a hydride selected from the group consisting of lithium aluminum hydride, sodium borohydride and NaBH$_3$CN at a temperature below that at which dimerization or oligomerization of the formylbenzocyclobutene compound or the thus-produced hydroxymethylbenzocyclobutene compound is a significant side reaction, for a time sufficient to convert the formylbenzocyclobutene compound to the hydroxymethylbenzocyclobutene compound, including the prior step of preparing a 3- or 4-formylbenzocyclobutene by reacting a substituted or unsubstituted 3- or 4-bromobenzocyclobutene compound with magnesium to produce a corresponding 3- or 4-benzocyclobutenyl magnesium bromide and treating the thus-formed 3- or 4-benzocyclobutenyl magnesium bromide with dimethylformamide to produce a corresponding 3- or 4-formylbenzocyclobutene compound.

2. The process of claim 1, wherein the formylbenzocyclobutene compound is 4-formylbenzocyclobutene.

3. The process of claim 1, wherein the hydride is sodium borohydride and reduction is carried out in an alcoholic solvent.

4. The process of claim 3, carried out in ethanol.

5. The process of claim 1, carried out at a temperature near ambient.

6. The process of claim 1, wherein the formylbenzocyclobutene compound is 4-formylbenzocyclobutene, the hydride is sodium borohydride and the process is carried out in ethanol at a temperature near ambient.

7. The process of claim 1, wherein hydride is lithium aluminum hydride and the solvent is diethyl ether or tetrahydrofuran.

8. The process of claim 1, wherein the formylbenzocyclobutene compound is 4-formylbenzocyclobutene, the hydride is lithium aluminum hydride and the process is carried out in diethyl ether at a temperature near ambient.

9. The process of claim 1, wherein the bromobenzocyclobutene compound is 4-bromobenzocyclobutene.

10. The process of claim 9, wherein 4-benzocyclobutenyl magnesium bromide is prepared from 4-bromobenzocyclobutene in tetrahydrofuran.

11. A process for preparing a substituted or unsubstituted 3- or 4-hydroxymethylbenzocyclobutene compound, comprising reducing a corresponding 3-or 4-formylbenzocyclobutene compound with a hydride selected from the group consisting of lithium aluminum hydride, sodium boro-hydride and NaBH$_3$CN at a temperature below that at which dimerization or oligomerization of the formylbenzocyclobutene compound or the thus-produced hydroxymethylbenzocyclobutene compound is a significant side reaction, for a time sufficient to convert the formylbenzocyclobutene compound to the hydroxymethylbenzocyclobutene compound, including the prior step of preparing a 3- or 4-formylbenzocyclobutene by reacting a benzocyclobutene compound and dichloromethyl methyl ether in the presence of titanium tetrachloride to produce the 3- or 4-formylbenzocyclobutene compound.

* * * * *